United States Patent [19]

Gregory

[11] 4,191,554
[45] Mar. 4, 1980

[54] HERBICIDAL BENZAMIDES
[75] Inventor: Walter A. Gregory, Wilmington, Del.
[73] Assignee: E. I. Du Pont de Nemours and Company, Wilmington, Del.
[21] Appl. No.: 838,958
[22] Filed: Oct. 3, 1977
[51] Int. Cl.² .................. C07C 103/80; C07D 295/18; A01N 9/20; A01N 9/22
[52] U.S. Cl. ............................................ 71/95; 71/98; 71/105; 71/115; 71/118; 71/121; 260/558 S; 260/559 R; 260/559 S; 260/326.5 E; 260/465 D; 260/453 RW
[58] Field of Search ............ 260/558 S, 559 B, 559 R, 260/559 S, 562 P, 517 E, 465 E, 326.5 J; 71/118, 115, 95, 105, 98, 121

[56] References Cited
U.S. PATENT DOCUMENTS

| | | | |
|---|---|---|---|
| 3,012,872 | 12/1961 | Richter | 71/118 X |
| 3,012,873 | 12/1961 | Richter | 71/118 X |
| 3,763,210 | 10/1973 | Heath et al. | 260/520 EX |
| 3,839,444 | 10/1974 | Theissen | 260/559 R |
| 4,063,929 | 12/1977 | Bayer et al. | 260/520 EX |

FOREIGN PATENT DOCUMENTS

| | | | |
|---|---|---|---|
| 240643 | 6/1965 | Austria | 71/115 |
| 48-27298 | 8/1973 | Japan | 260/559 R |
| 209445 | 1/1968 | U.S.S.R. | 260/559 R |

Primary Examiner—Arthur P. Demers

[57] ABSTRACT

Herbicidal compounds of the formula:

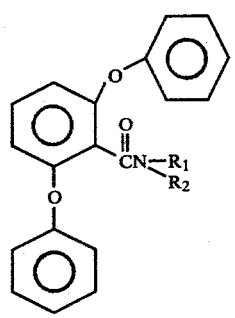

(I)

where
$R_1$ is hydrogen, methyl or ethyl;
$R_2$ is alkyl of 1–4 carbon atoms, methoxy or cyanomethyl; and pl $R_1$ and $R_2$ together can be —(CH$_2$)$_4$—, provided that when $R_2$ is alkyl of 3 or 4 carbon atoms, methoxy or cyanomethyl, $R_1$ cannot be ethyl.

21 Claims, No Drawings

HERBICIDAL BENZAMIDES

BACKGROUND OF THE INVENTION

Recently in U.S. Pat. No. 3,839,444 halophenoxybenzamide herbicides were described. The herbicides have the general formula

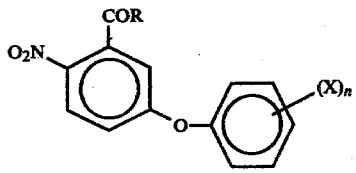

wherein

X is halogen, n is 1 to 5, and R is amido, alkylamido ($C_1$–$C_4$) or dialkylamido ($C_3$–$C_4$).

A continuing need exists for active herbicides; especially active herbicides which are selective. The presence of undesired vegetation is very damaging to useful crops such as rice. In the current world situation, wherein food shortages are quite acute, it is most important not to lose a significant portion of a valuable crop such as rice. The presence of such undesired vegetation results in the loss of a significant portion of such crop. Thus, a need exists for a particularly effective herbicide which will destroy as much of the unwanted vegetation as is possible without causing significant damage to the desired crops, e.g., rice.

According to the instant invention, herbicidal compounds have been discovered which are highly active herbicides and yet cause minimal damage to desired crops such as rice or wheat.

DESCRIPTION OF THE INVENTION

This invention relates to the novel compounds of Formula I and to agricultural compositions containing them, and to the method of use of these compounds as selective herbicides having both pre- and postemergence activity:

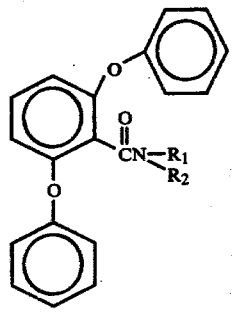

(I)

where $R_1$ is hydrogen, methyl, or ethyl;

$R_2$ is alkyl of 1–4 carbon atoms, methoxy or cyanomethyl; and $R_1$ and $R_2$ together can be —$(CH_2)_4$— provided that when $R_2$ is alkyl of 3 or 4 carbon atoms, methoxy or cyanomethyl, $R_1$ cannot be ethyl.

In particular these compounds are useful as herbicides for rice since they are effective against undesired vegetation and do minimal damage to the rice plant.

Preferred for their higher herbicidal activity or favorable cost or both are those compounds of Formula I where $R_1$ is methyl and $R_2$ is methyl or methoxy.

Specifically preferred for their outstanding herbicidal activity or highly favorable cost or both are: N-methoxy, N-methyl-2,6-diphenoxybenzamide and N,N-dimethyl-2,6-diphenoxybenzamide.

DETAILED DESCRIPTION OF THE INVENTION

Synthesis

The preparation of the compounds of this invention can be accomplished by first preparing 2,6-diphenoxybenzoic acid by any one of the following methods.

Method I

The desired 2,6-diphenoxybenzoic acid can be prepared as illustrated in equation 1

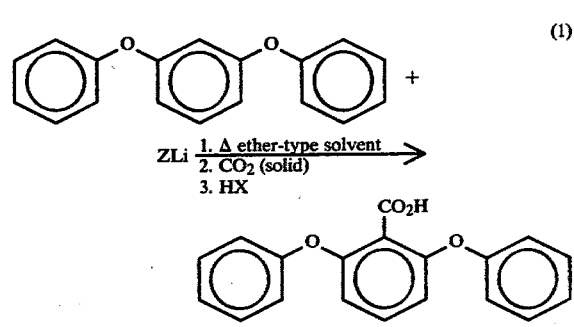

(1)

In this method, 1,3-diphenoxybenzene is caused to react with an alkyllithium compound ZLi where Z is alkyl of 1 to 4 carbon atoms or phenyl, for example, methyllithium or butyllithium, in an ether-type solvent such as diethyl ether or tetrahydrofuran for 0.5 to 3 hours at 25°–100°, preferably at the boiling point of the solvent. The resulting intermediate, 2,6-diphenoxyphenyllithium, is added to an excess of solid carbon dioxide, or a mixture of solid carbon dioxide in ether, and the mixture is allowed to warm to room temperature to yield lithium 2,6-diphenoxybenzoate. Addition of a mineral acid, HX, such as hydrochloric acid or sulfuric acid, yields 2,6-diphenoxybenzoic acid.

Method II

Alternatively, 2,6-diphenoxybenzoic acid can be made as illustrated in Equation 2:

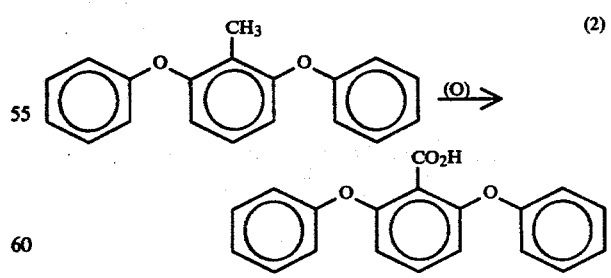

(2)

In this method, 2,6-diphenoxytoluene is converted to the benzoic acid by means of an appropriate oxidizing agent, such as potassium permanganate, potassium dichromate, or air.

The starting materials in Equations 1 and 2, namely 1,3-diphenoxybenzene and 2,6-diphenoxytoluene, are prepared by treating the disodium salts of resorcinol and 2-methylresorcinol, respectively, with bromobenzene in pyridine at 110°–120° C., in the presence of cuprous chloride.

The compounds of this invention can be prepared by established procedures making use of intermediary 2,6-diphenoxybenzoyl chloride which is in turn made by treating the acid with thionyl chloride or oxalyl chloride. See A. I. Vogel, "A Textbook of Practical Organic Chemistry", John Wiley and Sons, Inc., New York, N.Y., 1965, page 361.

The interaction of 2,6-diphenoxybenzoyl chloride with amines in a suitable solvent such as tetrahydrofuran, methylene chloride, pyridine, etc. in the presence of an acid acceptor such as excess amine, pyridine, triethylamine, etc. gives the desired benzamides.

This conversion can be more clearly understood by reference to the following equations where $R_1$ and $R_2$ have the same values as in formula I.

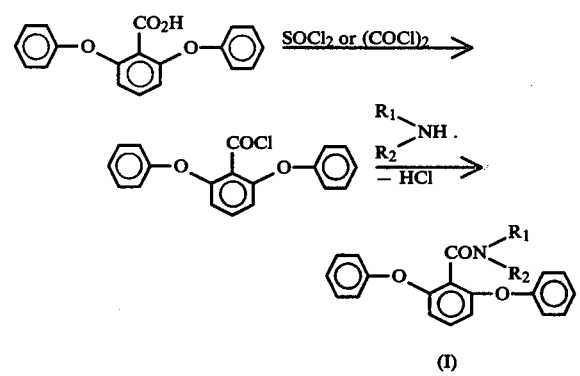

(I)

PREPARATION

In order that the invention may be better understood, the following examples are provided.

Unless otherwise indicated all parts are by weight and all temperatures in °C.

EXAMPLE I 2,6-Diphenozybenzoic Acid

To a mixture of 11 parts of 1,3-diphenoxybenzene and 40 parts of tetrahydrofuran is added 1 part of methyllithium (as a 1.82 M solution in diethyl ether) while the mixture is cooled in an ice bath. The resulting solution is heated under reflux for 2 hours and then is poured slowly onto 500 parts of dry ice. After the mixture has warmed to room temperature, 100 parts of water are added, and the tetrahydrofuran is evaporated. After the aqueous solution is extracted with 50 parts diethyl ether, it is then acidified with concentrated hydrochloric acid. The white solid which forms is collected to yield 12 parts of 2,6-diphenoxybenzoic acid. The compound is purified by recrystallization from acetonitrile to give 8 parts of pure material, M.P. 164°–165°.

EXAMPLE II 2,6-Diphenoxytoluene

A mixture of 4 parts of 2-methylresorcinol, 7 parts of potassium tert-butoxide, 11 parts of bromobenzene, 1 part cuprous chloride and 70 parts of pyridine is distilled until the temperature reaches 115°, and then is heated under reflux for 15 hours. The mixture is then added to 100 parts of ice water, made acidic with concentrated hydrochloric acid and extracted several times with toluene. The toluene extracts are dried over anhydrous potassium carbonate, concentrated and distilled to give 2,6-diphenoxytoluene, B.P. 146°–156° (0.2 torr), M.P. 39°–41°.

EXAMPLE III 2,6-Diphenoxybenzoic Acid

A mixture of 1 part of 2,6-diphenoxytoluene, 7 parts of pyridine and 15 parts of water is warmed to 50° C. With vigorous stirring, 2 parts of potassium permanganate are added, and the heating and stirring are continued for 4 hours. After being allowed to stand for 15 hours, the mixture is filtered, and the filter cake is washed with dilute aqueous sodium hydroxide and water. After the combined filtrate and washings are extracted with diethyl ether, they are made acidic with concentrated hydrochloric acid. The crystals which separate are 2,6-diphenoxybenzoic acid, M.P. 162°–164°, which, after recrystallization from acetonitrile, melt at 164°–165.5°.

EXAMPLE IV 2,6-Diphenoxybenzoyl Chloride

Fifteen parts of thionyl chloride or oxalyl chloride are added to 2 parts of 2,6-diphenoxybenzoic acid. The mixture is heated under reflux for 30 minutes, and the excess chloride is distilled. The residue crystallizes to give 2,6-diphenoxybenzoyl chloride, M.P. 72°–73°.

EXAMPLE V

N,N-Dimethyl-2,6-diphenoxybenzamide

To 18 parts of pyridine which has been saturated with dry gaseous dimethylamine is added dropwise 1 part of 2,6-diphenoxybenzoyl chloride in 2 parts of pyridine. The resulting mixture is stirred for 30 minutes, concentrated under reduced pressure, and poured into 54 parts of water. The mixture is made acidic with concentrated hydrochloric acid, and the solid precipitate is collected, washed with water, dried, and recrystallized first from acetonitrile and then from 1-chlorobutane to give N,N dimethyl-2,6-diphenoxybenzamide, M.P. 109°–111°.

The following compounds can be prepared from equimolar amounts of 2,6-diphenoxybenzoyl chloride and the appropriate amine as described in Example V.

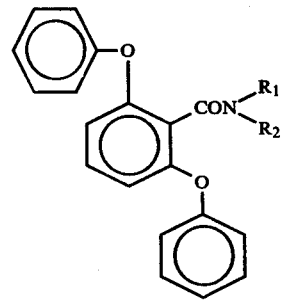

| $R_1$ | $R_2$ |
| --- | --- |
| H | $CH_3-$ |
| H | $CH_3O-$ |
| H | $C_2H_5-$ |
| H | $n-C_3H_7-$ |
| H | $iso-C_3H_7-$ |
| H | $n-C_4H_9-$ |
| H | $sec-C_4H_9-$ |
| H | $iso-C_4H_9-$ |

-continued

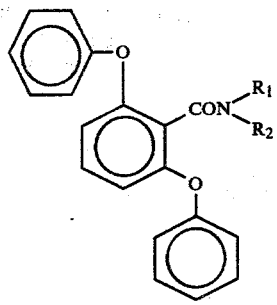

| R₁ | R₂ |
|---|---|
| H | t-C₄H₉— |
| H | NCCH₂— |
| CH₃— | CH₃O— |
| CH₃— | C₂H₅— |
| CH₃— | n-C₃H₇— |
| CH₃— | iso-C₃H₁— |
| CH₃— | n-C₄H₉— |
| CH₃— | sec-C₄H₉— |
| CH₃— | iso-C₄H₉— |
| CH₃— | t-C₄H₉— |
| CH₃— | NCCH₂— |
| C₂H₅— | C₂H₅— |
| —(CH₂)₄— | |

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Percent by Weight | | |
|---|---|---|---|
|  | Active Ingredient | Diluent | Surfactant (s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5 line 43 through Col. 7, line 62 and Ex. 8, 12, 15, 39, 41, 52, 53, 58, 132, 138–140, 162–164, 166, 167, 169–182.

H. Gysin and E. Knüsli, U.S. Pat. No. 2,891,855, June 23, 1959, Col. 3, line 66 through Col. 5, line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE VI

| Wettable Powder | |
|---|---|
| N,N-Dimethyl-2,6-Diphenoxybenzamide | 50% |
| sodium alkylnaphthalenesulfonate | 2% |
| low viscosity methyl cellulose | 2% |
| diatomaceous earth | 46% |

The ingredients are blended, coarsely hammermilled and then air milled to produce particles of active essentially all below 10 microns in diameter. The product is reblended before packaging.

EXAMPLE VII

| Granule | |
|---|---|
| wettable powder of Example VI | 15% |
| gypsum | 69% |
| potassium sulfate | 16% |

The ingredients are blended in a rotating mixer and water sprayed on to accomplish granulation. When most of the material has reached the desired range of 1.0 to 0.42 mm. (U.S.S. #18 to 40 sieves), the granules are removed, dried, and screened. Oversize material is crushed to produce additional material in the desired range. These granules contain 7.5% active ingredient.

EXAMPLE VIII

| Emulsifiable Concentrate | |
| --- | --- |
| N,N-Dimethyl-2,6-diphenoxybenzamide | 30% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE IX

| Aqueous Suspension | |
| --- | --- |
| N,N-Dimethyl-2,6-diphenoxybenzamide | 50.0% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| water | 46.7% |

The ingredients are ground together in a sand mill to produce particles essentially all under five microns in size.

Utility

The compounds of the present invention are useful for the selective control of undesired vegetation in cereal crops such as rice and wheat, and other crops such as soybeans. More particularly, the compounds of the present invention can be used for the control of weeds in paddy rice. These compounds are especially effective for preemergence weed control, but they also can be used for postemergence weed control.

The compounds of this invention are useful for the control of weeds in transplanted crops such as rice, tobacco, tomatoes, cabbage, sweet potatoes, lettuce, celery, peppers, and eggplant. The treatment may be applied to the soil surface prior to transplanting and the crop transplanted through the treated soil or it may be soil incorporated prior to transplanting and the crop set in the treated soil. It may also be applied after the crop is transplanted although care should be taken to keep the chemical off the crop.

The precise amount of the compounds of the present invention to be used in any given situation will vary according to the particular end result desired, the use involved, the crop and weed species, and soil involved, the formulation used, the mode of application, prevailing weather conditions, foliage density and the like factors. Since so many variables play a role, it is not possible to state a rate of application suitable for all situations. Broadly speaking, the compounds of the invention are used at levels of about 0.03 to about 15 kilograms, preferably about 0.5 to about 10 kilograms per hectare. The lower rates in this range will generally be selected on lighter soils, soils low in organic matter content, or in situations where maximum persistence is not necessary.

Although the compounds of the present invention provide excellent weed control when applied as the sole herbicide treatment, they may be advantageously applied in combination with other herbicides, including, but not restricted to, the following:

3-chloro-2-(4-chloro-2-fluorophenyl)-4,5,6,7-tetrahydro-2H-indazole
5-tert-butyl-3-(2,4-dichloro-5-isopropoxyphenyl)-1,3,4-oxadiazol-2-one
S-(4-chlorobenzyl)-N,N-diethylthiolcarbamate
2,4-dichlorophenyl-3'-methoxy-4'-nitrophenyl ether
2-chloro-2',6'-diethyl-N-butoxymethylacetanilide
2-methylthio-4,6-bis(ethylamino)-S-triazine
S-ethyl hexahydro-1H-azepine-1-carbothioate
3-isopropyl-1(H)-benzo-2,1,3-thiadiazin-4-one-2,2-dioxide
2,4-dichlorophenoxyacetic acid and closely related derivatives including salts The herbicidal activity of the compounds of this invention was discovered in greenhouse tests, conducted as described below.

Procedure Test 1

Seeds of crabgrass (*Digitaria* spp.), barnyardgrass (*Echinochloa crusgalli*), wild oats (*Avena fatua*), Cassia tora, morningglory (*Ipomoea* spp.), cocklebur (*Xanthium* spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

The ratings for compounds tested by this procedure are recorded in Table 1, and consist of a number and a letter. The number describes the extent of the response and ranges from zero to ten, with zero representing no response and ten representing 100% response. The letter describes the type of response, with "B" representing burn (acute response), "C" chlorosis-necrosis (chronic response), "E" emergence inhibited, "G" growth retarded, "H" formative effect (malformation or hormone type), and "L" representing lodging.

TABLE 1

| | | | | | | | POST EMERGENCE | | | | | | | |
| --- | --- | --- | --- | --- | --- | --- | --- | --- | --- | --- | --- | --- | --- | --- |
| COMPOUND | Kg per Hectare | Bush Bean | Cotton | Morning Glory | Cocklebur | Cassia | Nutsedge | Crabgrass | Barnyard Grass | Wild Oats | Wheat | Corn | Soybean | Rice | Sorghum |

TABLE 1-continued
| COMPOUND | Kg/Hectare | | | | | | | | | | | | | | |
|---|---|---|---|---|---|---|---|---|---|---|---|---|---|---|---|
| 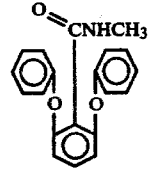 O=CNHCH₃ | 2 | 0 | 0 | 0 | 3B | 1B | 0 | 5G | 8C | 0 | 0 | 0 | 2G | 0 | 5G |
| 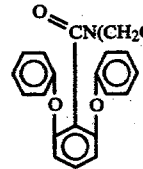 O=CN(CH₂CH₃)₂ | 2 | 0 | 0 | 1B | 1B | 1B | 0 | 0 | 4C | 0 | 0 | 1B | 1B | 0 | 0 |
| 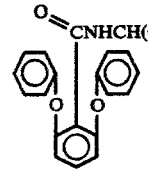 O=CNHCH(CH₃)₂ | 2 | 0 | 0 | 0 | 0 | 0 | 0 | 0 | 0 | 0 | 0 | 0 | 0 | 0 | 0 |
| 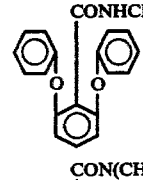 CONHCH₂CH₃ | 2 | 0 | 0 | 0 | 0 | 0 | 0 | 0 | 0 | 0 | 0 | 0 | 0 | 0 | 0 |
| 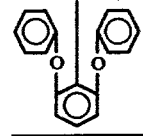 CON(CH₃)₂ | 2 | 8G | 0 | 2G | 0 | 3H | 5G | 0 | 4C 6H | 0 | 0 | 4G | 1B | 0 | 0 |
| | | | | | | PRE-EMERGENCE | | | | | | | | |
|---|---|---|---|---|---|---|---|---|---|---|---|---|---|---|
| COMPOUND | Kg/Hectare | Morning Glory | Cockle-bur | Nut-Cassia | Crab-sedge | Barn-yard grass | Wild Grass | Oats | Wheat | Soy-Corn | bean | Sor-Rice | ghum | |
|  O=CNHCH₃ | 2 | 2C | 3C | 3C | 8G | 8G | 4C 9G | 8C | 9G | 3C 6G | 0 | 5C | 7H | |
| 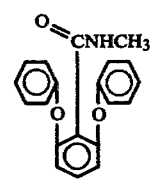 O=CN(CH₂CH₃)₂ | 2 | 1C | 1H | 1H | 0 | 2G | 7C | 2C | 1H | 4G | 0 | 1C | 0 | |
| 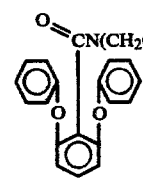 O=CNHCH(CH₃)₂ | 2 | 2H | 0 | 2H | 0 | 0 | 6G | 0 | 0 | 2G | 0 | 0 | 2H | |
| 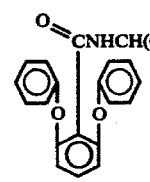 CONHCH₂CH₃ | 2 | 0 | 10E | 0 | 0 | 2G | 9C | 5G | 7G | 1C 5G | 0 | 1C | 0 | |

TABLE 1-continued

| | | | | | | | | | | | | | |
|---|---|---|---|---|---|---|---|---|---|---|---|---|---|
| CON(CH$_3$)$_2$ 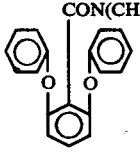 | 2 | 4G | 3G | 3G | 10E | 7G | 10C | 3C 7G | 8G | 2C 7G | 2G | 5C | 2C 7G |

The following table, Table 2, is presented to further illustrate the biological activity of the compounds of this invention. The data illustrate the herbicidal efficacy of the compounds with selectivity for two important crops, rice and wheat.

The test compounds were applied in a nonphytotoxic solvent to soil pots containing seeds of an intermediate hybrid rice, japonica rice, barnyardgrass (*Echinochloa crusgalli*), and morningglory (*Ipomoea* sp.). In addition, seeds of wheat, wild oats (*Avena fatua*), downy brome (*Bromus tectorum*), and cheat (*Bromus secalinus*) were included in some tests, as were established plantings (postemergence) of some or all of the species mentioned above. The plants were maintained in a greenhouse (glasshouse), and visual plant response ratings (as described in Table 1) were generally taken three to four weeks after application.

Table 2

| Compound | kg ai/ha | Preemergence | | | | | | | | Postemergence | | | | | | |
|---|---|---|---|---|---|---|---|---|---|---|---|---|---|---|---|---|
| | | Inter-mediate Rice | Japonica Rice | Barn-yard-grass | Morn-ing-glory | Wheat | Wild Oats | Bromus tectorum | Bromus secalinus | Inter-mediate Rice | Japonica Rice | Barn-yard-grass | Morn-ing-glory | Wheat | Wild Oats | Bromus tectorum | Bromus secalinus |
| O=CNHCH₃ / (2,6-diphenoxyphenyl) | ½ | 0 | 0 | 8C | 0 | | | | | 0 | 0 | 0 | 0 | | | | |
| | 2 | 0 | 0 | 9C | 10C | | | | | 0 | 0 | 0 | 0 | | | | |
| O=CN(CH₂CH₃)₂ / (2,6-diphenoxyphenyl) | ½ | 0 | 0 | 1C | 0 | 0 | 0 | 0 | 0 | | | | | | | | |
| | 2 | 0 | 0 | 7C | 0 | 0 | 0 | 3C | 3C | | | | | | | | |
| O=CNHCH₂CH₃ / (2,6-diphenoxyphenyl) | ½ | 0 | 0 | 5E | 0 | | | | | | | | | | | | |
| | 2 | 0 | 0 | 9C | 0 | | | | | | | | | | | | |
| O=CN(CH₃)₂ / (2,6-diphenoxyphenyl) | ½ | 0 | 0 | 5G | 0 | 0 | 0 | 2G | 0 | 0 | 0 | 0 | 0 | 0 | 0 | 0 | 0 |
| | ¼ | 0 | 0 | 7G | 0 | 0 | 0 | 2G | 2G | 0 | 0 | 0 | 0 | 0 | 0 | 0 | 0 |
| | | 0 | 0 | 9L | | | | | | | | | | | | | |
| | ½ | 0 | 0 | 10C | 0 | 0 | 0 | 5G | 2G | 1C | 1G | 1C | 0 | 0 | 0 | 1G | 3G |
| | 1 | 0 | 1G | 10C | 0 | 0 | 0 | 5G | 9G | 1C | 1G | 1G | 0 | 0 | 0 | 3G | 3G |
| | | | | | | | | | 3C | | | | | | | | |

It should be noted that these compounds at a low concentration virtually eliminated the undesirable vegetation, e.g., barnyardgrass, but had relatively little effect on the crops, e.g., rice.

The following table, Table 3, is presented to additionally illustrate the biological activity of the compounds of the present invention. The data illustrate the herbicidal efficacy of the compounds with selectivity for rice in paddy culture.

A rice paddy was constructed using a tub containing soil and barnyardgrass (*Echinochloa crusgalli*) seeds, and japonica rice plants which were transplanted into the paddy soil when in the three to four leaf stage. The water level was maintained a few centimeters above the soil surface. The test sample was applied directly into the paddy water, and plant response ratings were taken about three weeks later.

TABLE 3

| Compound | Rate, kg ai/ha | Japonica Rice | Barnyardgrass |
|---|---|---|---|
| 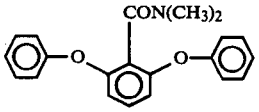 | 1/32 | 0 | 9C |
| | 1/16 | 0 | 10C |
| | ⅛ | 0 | 10C |
| | ¼ | 0 | 10C |

What is claimed is:

1. A compound of the formula:

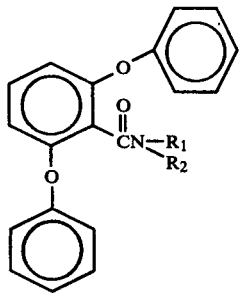

where
$R_1$ is hydrogen, methyl, or ethyl;
$R_2$ is alkyl of 1-4 carbon atoms, methoxy or cyanomethyl; and
$R_1$ and $R_2$ together can be —$(CH_2)_4$—, provided that when $R_2$ is alkyl of 3 or 4 carbon atoms, methoxy or cyanomethyl, $R_1$ cannot be ethyl.

2. A compound of claim 1 wherein $R_1$ is methyl.

3. A compound of claim 2 wherein $R_2$ is methyl or methoxy.

4. The compound of claim 1, N-methoxy, N-methyl-2,6-diphenoxybenzamide.

5. The compound of claim 1, N,N-dimethyl-2,6-diphenoxybenzamide.

6. A composition for the control of undesirable vegetation consisting essentially of a compound of claim 1 and at least one of (a) a surface-active agent and (b) a solid or liquid diluent.

7. A composition for the control of undesirable vegetation consisting essentially of a compound of claim 2 and at least one of (a) a surface-active agent and (b) a solid or liquid diluent.

8. A composition for the control of undesirable vegetation consisting essentially of a compound of claim 3 and at least one of (a) a surface-active agent and (b) a solid or liquid diluent.

9. A composition for the control of undesirable vegetation consisting essentially of the compound of claim 4 and at least one of (a) a surface-active agent and (b) a solid or liquid diluent.

10. A composition for the control of undesirable vegetation consisting essentially of the compound of claim 5 and at least one of (a) a surface-active agent and (b) a solid or liquid diluent.

11. A method for the control of undesirable vegetation comprising applying to the locus of such undesirable vegetation a herbicidally effective amount of a compound of claim 1.

12. A method for the control of undesirable vegetation comprising applying to the locus of such undesirable vegetation a herbicidally effective amount of a compound of claim 2.

13. A method for the control of undesirable vegetation comprising applying to the locus of such undesirable vegetation a herbicidally effective amount of a compound of claim 3.

14. A method for the control of undesirable vegetation comprising applying to the locus of such undesirable vegetation a herbicidally effective amount of the compound of claim 4.

15. A method for the control of undesirable vegetation comprising applying to the locus of such undesirable vegetation a herbicidally effective amount of the compound of claim 5.

16. A method for the control of barnyardgrass in rice comprising applying to the locus of such barnyardgrass a herbicidally effective amount of a compound of claim 1.

17. A method for the control of barnyardgrass in rice comprising applying to the locus of such barnyardgrass a herbicidally effective amount of a compound of claim 2.

18. A method for the control of barnyardgrass in rice comprising applying to the locus of such barnyardgrass a herbicidally effective amount of a compound of claim 3.

19. A method for the control of barnyardgrass in rice comprising applying to the locus of such barnyardgrass a herbicidally effective amount of the compound of claim 4.

20. A method for the control of barnyardgrass in rice comprising applying to the locus of such barnyardgrass a herbicidally effective amount of the compound of claim 5.

21. A method of claim 16 wherein the rice is paddy rice.

* * * * *